United States Patent [19]
Saby

[11] Patent Number: 6,012,019
[45] Date of Patent: Jan. 4, 2000

[54] PROCESS FOR TRACKING AND MONITORING A MANUFACTURING UNIT AND/OR A NEAR-INFRARED SPECTROMETER BY MEANS OF AT LEAST ONE CRITERION OF QUALITY OF SETS OF SPECTRA

[75] Inventor: Claude-Alain Saby, Bron, France

[73] Assignee: Elf Antar France, Courbevoie, France

[21] Appl. No.: 08/956,436

[22] Filed: Oct. 23, 1997

[30] Foreign Application Priority Data

Oct. 23, 1996 [FR] France .................................. 96 12917

[51] Int. Cl.[7] ............................ G01N 21/31; G06F 17/00
[52] U.S. Cl. ........................ 702/32; 702/30; 250/339.07; 250/339.12
[58] Field of Search .................................. 702/32, 30, 28, 702/27, 85; 250/339.07, 339.08, 339.12, 495.1, 504 R

[56] References Cited

U.S. PATENT DOCUMENTS

| | | | |
|---|---|---|---|
| 5,121,337 | 6/1992 | Brown ........................................ | 702/28 |
| 5,446,681 | 8/1995 | Gethner et al. ........................... | 702/27 |
| 5,452,232 | 9/1995 | Espinosa et al. ......................... | 702/30 |
| 5,475,612 | 12/1995 | Espinosa et al. ......................... | 702/30 |
| 5,708,593 | 1/1998 | Saby et al. ................................ | 702/85 |
| 5,712,797 | 1/1998 | Descales et al. ......................... | 702/30 |

*Primary Examiner*—Marc S. Hoff
*Assistant Examiner*—Bryan Bui
*Attorney, Agent, or Firm*—Oblon, Spivak, McClelland, Maier & Neustadt, P.C.

[57] ABSTRACT

A process for tracking and monitoring the operation of a unit for manufacturing a product and/or a near-infrared spectrometer fed with the product. The process includes periodically recording spectra arising from the near-infrared spectrometer, mathematically transforming the spectra, computing at least one quality criterion, intercomparing two sets of spectra after transformation, and tracking the evolution of this criterion over time. The process finds its application in the chemical, petroleum, pharmaceutical, cosmetological, and agro-food industries.

20 Claims, 2 Drawing Sheets

PROCESS FOR TRACKING AND MONITORING A MANUFACTURING UNIT AND/OR A NEAR-INFRARED SPECTROMETER BY MEANS OF AT LEAST ONE CRITERION OF QUALITY OF SETS OF SPECTRA

TECHNICAL FIELD

The present invention relates to an on-line process for tracking and monitoring a manufacturing unit with the aid of the spectra arising from a near-infrared spectrometer to which it is linked. The process of the invention also allows the tracking and monitoring of the spectrometer itself.

It finds its application in the chemical, petroleum, pharmaceutical, cosmetological and agro-food industries.

STATE OF THE PRIOR ART

The near-infrared spectrometers used to determine physical or chemical characteristics of a sample of product to be analysed have to calibrated.

Calibration consists in devising a model which represents the mathematical relation between a characteristic of the product to be analysed and the spectrum delivered by the spectrometer. The model is built by implementing multivariate statistical techniques such as principal component analysis, principal component regression, partial least squares regression or neural networks.

Known methods of tracking and monitoring manufacturing units or near-infrared spectrometers consist in selecting either certain elements of the spectrum, or variables arising from the computations of the modelling, and then in tracking these elements and/or these variables by means of control charts.

One of these known methods is described in French Patent Application No. 95 12087 filed on Oct. 16, 1995. This method of tracking the operation of a slave instrument and of a manufacturing unit to which it is linked comprises a procedure of multivariate calibration of a master analyser, periodic procedures for standardizing the signals delivered by the slave analyser fed with the standardizing products and a calibration transfer step during which parameters associated with a calibration transfer algorithm are computed. It consists furthermore in choosing, on the one hand, at least one of parameters or a mathematical combination of at least two of them as tracking and control indicator for the operation of the slave analyser and on the other hand a method of tracking and control. At the completion of each periodic standardizing procedure, the evolution over time of the value of the tracking and control indicator is monitored by applying the tracking and control method, then proper operation of the slave analyser and that of the manufacturing unit to which it is linked is ascertained by identifying the causes of the evolution of the value of the indicator from the results obtained by applying the tracking and control method and a causes/effects diagram. According to a particular characteristic of this method, the slave analyser and the master analyser are the same analyser used at different periods of time.

This method is particularly well suited to the tracking of near-infrared spectrometers. On the other hand, it does not always make it possible to distinguish the changes of production from the malfunctions of the unit to which these spectrometers are linked. It also has the drawback of requiring standardizing products and transfer tables which are difficult to manipulate.

BACKGROUND OF THE INVENTION

The present invention is aimed specifically at remedying these drawbacks, and in particular at providing a process for tracking and/or monitoring the operation of a near-infrared spectrometer and the manufacturing unit to which it is linked.

By virtue of this process it is possible to expose disturbances, drifting, anomalies of operation of the spectrometer and of the associated measurement rig as well as of the manufacturing unit to which it is linked, to identify the causes of these malfunctions and to make provisions suitable for each situation: for example to declare the result of an analysis invalid and to warn the operator running the unit to which the spectrometer is linked and to supply him with elements for making his decisions.

This process finds its application in analysis laboratories and the manufacturing units of the chemical, petroleum, pharmaceutical, cosmetological and agro-food industries.

For this purpose the present invention proposes a process for tracking and monitoring the operation of a unit for manufacturing a product and/or a near-infrared spectrometer fed with the product, the said spectrometer delivering spectra consisting of series of values of absorbance for various values of wavelengths, consisting in executing the following steps:

periodically recording, in the form of numerical data, spectra arising from the near-infrared spectrometer, mathematically transforming the numerical data of each recorded spectrum so as to obtain transformed spectra, characterized in that it consists in executing the following steps also:

constructing a string of work spectra from the values previously obtained, by choosing wavelengths in each transformed spectrum, by a method of selection, selecting from the string of work spectra, a first set of work spectra containing from 20 to 50 consecutive spectra, selecting from the string of work spectra, a second set of work spectra, of the same dimension as the first set, the spectra being consecutive and shifted in time with respect to the spectra of the first set, computing at least one quality criterion so as to intercompare the first and second sets of spectra, tracking the evolution of the quality criterion over time.

According to another characteristic of the invention, the method of selection of the wavelengths of the work spectra is chosen from among the method of stepwise selection, the method of selection by elimination, a method applying a regression algorithm and a method implementing genetic algorithms.

According to another characteristic of the invention, the first set of work spectra comprises spectra obtained from reference products with known characteristics.

According to another characteristic of the invention, the first set of work spectra containing a first spectrum, the second set of work spectra consists of the same spectra as the first set, except for the first which is replaced with a spectrum not belonging to the first set.

According to another characteristic of the invention, the spectra of the first and second sets of work spectra being made up of numerical data, the quality criterion is a criterion of representativity of data, which implements a metric characterizing a distance between the said sets.

According to another characteristic of the invention, the spectra of the first and second sets of work spectra being made up of numerical data, the quality criterion is a first criterion of homogeneity of the said data comparing on the one hand the shapes and on the other hand the orientations of the said sets.

According to another characteristic of the invention, the spectra of the first and second sets of work spectra being made up of numerical data, the quality criterion is a second criterion of homogeneity of the data intercomparing the densities of the said numerical data.

According to another characteristic of the invention, the quality criterion is a global criterion computed via a formula involving at least two criteria chosen from among the criterion of representativity, the first criterion of homogeneity and the second criterion of homogeneity.

According to another characteristic of the invention, in order to track the evolution over time of the quality criterion, a monovariate control chart is used.

According to another characteristic of the invention, in order to track the evolution over time of the quality criterion, a causes/effects diagram is used.

BRIEF DESCRIPTION OF THE DRAWINGS

The invention will be better understood on reading the description which follows, with reference to the appended drawings in which.

DETAILED ACCOUNT OF THE INVENTION

Figure 1:
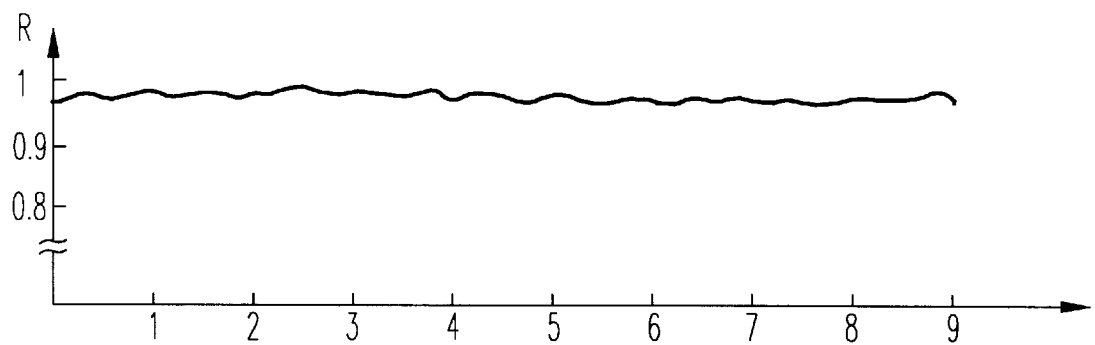
FIG. 1 represents the evolution over time of a criterion of representativity of the first and second sets of work spectra.

Generally, the process of the invention makes it possible to track and monitor the operation of a manufacturing unit by means of a near-infrared spectrometer. It also allows the tracking and monitoring of the operation of the spectrometer itself used to determine a physical characteristic of the manufactured product, a sample of which is fed to the spectrometer.

The process of the invention used to monitor the proper operation of a production unit, for example the production of petrol in a crude oil refinery, consists in periodically recording in a computer every three minutes, in the form of numerical data, the results of the measurement of absorbance of the petrol produced, by means of a near-infrared spectrometer, in the 907 nm to 1793 nm range. With a sampling spacing of 0.75 nm a set of spectra each consisting of the 1182 absorbance values measured over this range of wavelengths is thus obtained. Each spectrum is then transformed by computing the first derivative of the absorbance with respect to wavelength.

The next step of the process of the invention consists in constructing a string of work spectra from the values obtained in the previous step by selecting from each transformed spectrum, wavelengths by means of the partial least squares method of regression which consists in executing the following procedures:

constructing a set of 50 derived spectra with which are associated the values of the sought-after characteristic, i.e. in our example, the engine octane number of the petrol produced, modelling the characteristic on the basis of the 50 derived spectra by using the method of decomposition by partial least squares, selecting wavelengths according to the magnitude of the values of the eigenvectors of the significant principal components arising from the decomposition.

13 wavelengths are thus selected: 1139.63 nm, 1155.28 nm, 1170.00 nm, 1185.38 nm, 1201.13 nm, 1209.38 nm, 1216.13 nm, 1360.13 nm, 1375.88 nm, 1400.00 nm, 1417.88 nm, 1431.00 nm, 1450.00 nm.

Each spectrum arising from a periodic recording is subjected to these differentiation and selection procedures so as to construct a string of work spectra.

The next step of the process of the invention consists in selecting from the string of work spectra, a first set of 30 consecutive spectra of 13 wavelengths corresponding to the spectra recorded at the instants $t_1$ to $t_{30}$.

A second set of 30 consecutive spectra of 13 wavelengths corresponding to the spectra recorded at times t2 to t31 is then selected from the string of work spectra.

The first and second sets of work spectra are intercompared by means of a representativity criterion R and of two homogeneity criteria P and C defined and computed in the following manner.

The representativity criterion R represents a distance between the two sets of spectra according to the MAHALANOBIS metric. It is computed for each pair of spectra from the first and second sets, according to the following formula:

$$R(sec, fir) = \frac{D_t - D(sec, fir)}{D_t}$$

in which,

R(sec, fir) is a criterion of representativity between the two sets of spectra first and second, $D_t$ is the MAHALANOBIS distance for a Fisher law, D(sec, fir) is the theoretical MAHALANOBIS distance between the two sets of spectra first and second.

R is interpreted in the following manner:

if R=0 the two sets are not representative of one another, if R=1 the two sets merge, the nearer to 1 is the value of R the more the two sets are representative of one another, the nearer to 0 is the value of R the less the sets are representative of one another.

The criterion P represents a first criterion of homogeneity of the sets of work spectra first and second, and it is determined by the following formula:

$$P(sec, fir) = \frac{\sum_{i=1}^{m} S_{sec}(i) \cdot S_{fir}(i)}{\sqrt{\sum_{i=1}^{m} S_{sec}^2(i) \cdot \sum_{i=1}^{m} S_{fir}^2(i)}}$$

in which:

P(sec, fir) is a criterion of homogeneity of the first and second sets of work spectra, $S_{sec}$ is the sum of the eigenvectors, weighted by the eigenvalues of the second set of work spectra, $S_{fir}$ is the sum of the eigenvectors, weighted by the eigenvalues of the first set of work spectra, m is the number of variables equal to 13, i varies from 1 to m, P is interpreted in the following manner:

if P=0 the two sets are not homogeneous, of P=1 the two sets have the same spread in space, the closer to 1 is the value of P the more homogeneous are the sets, the closer to 0 is the value of P the less homogeneous are the sets, P expresses the spatial distribution of the data by comparing the shapes and orientations of the sets of work spectra. It has been determined experimentally that if P<0.7 the two sets are not homogeneous.

The criterion C represents a second criterion of homogeneity of the first and second sets of work spectra, and it is determined by the following formula:

$$C(sec, fir) = \exp\left[\frac{-M(sec, fir)}{(n_{sec}-1)+(n_{fir}-1)}\right]$$

in which:

$C_{(fir, sec)}$ is a second criterion of homogeneity of the first and second sets, $n_{fir}$ is the number of spectra in the first set, $n_{sec}$ is a number of spectra in the second set, $M_{(fir, sec)}$ is itself defined by the formula, $$M(\text{fir, sec}) = v[(n_{fir}-1) \cdot \log|A_{fir}^{-1}A| + (n_{sec}-1)\log|A_{sec}^{-1}A|]$$

in which:

$|.|$ is a determinant.

$$v = 1 - \frac{2p^2+3p-1}{6(p+1)}\left(\frac{1}{n_{fir}-1}+\frac{1}{n_{sec}-1}-\frac{1}{n_{fir}+n_{sec}-2}\right)$$

and in which:

P is the number of variables equal to 13.

$A_{fir}$ is the variance covariance matrix of the first set, $A_{sec}$ is the variance-covariance matrix of the second set, A is the variance-covariance matrix of the set of observations of the first and second sets, C is interpreted in the following manner:

if C=0 the covariances of the first and second sets are different, if C=1 the covariances of the first and second sets are equal, the nearer to 1 is the value of C, the nearer are the covariances and the more homogeneous are the groups, the nearer to 0 is the value of C, the less homogeneous are the groups.

A global quality criterion F, defined piecewise as a function of P is computed in the following manner:

$$\text{If } P \in [-1, 0.6[ \text{ then } F = \frac{1}{2} \times P \times \sqrt{\frac{C^2+R^2}{2}}$$

$$\text{If } P \in [0.6, 0.7[ \text{ then } F = (4P-2, 1) \times \sqrt{\frac{C^2+R^2}{2}}$$

$$\text{If } P \in [0.7, 1] \text{ then } F = P \times \sqrt{\frac{C^2+R^2}{2}}$$

The global criterion F thus computed, lying between −0.5 and 1, is normalized between 0 and 1 by linear interpolation.

A value of F close to 1 indicates that the two sets of work spectra are homogeneous and representative.

It is considered that the first set corresponds to a window of aperture 30 and that the second set corresponds to the same window with a sliding with a spacing of 1.

The process of the invention then consists in sliding the window over time and in computing the quality criteria R, P and C at the times ti and ti+1. The values thus obtained are represented in FIGS. 1, 2 and 3 respectively.

In FIG. 1 it is observed that the representativity criterion R is substantially constant and close to 1, this signifying that the experimental domain, that is to say the range of variation of the values of the new spectra introduced into the second set of work spectra, is the same as that of the previous spectra. Were the value of R to deviate from 1 this would signify that the experimental domain is not the same as that of the previous spectra.

Figure 2:
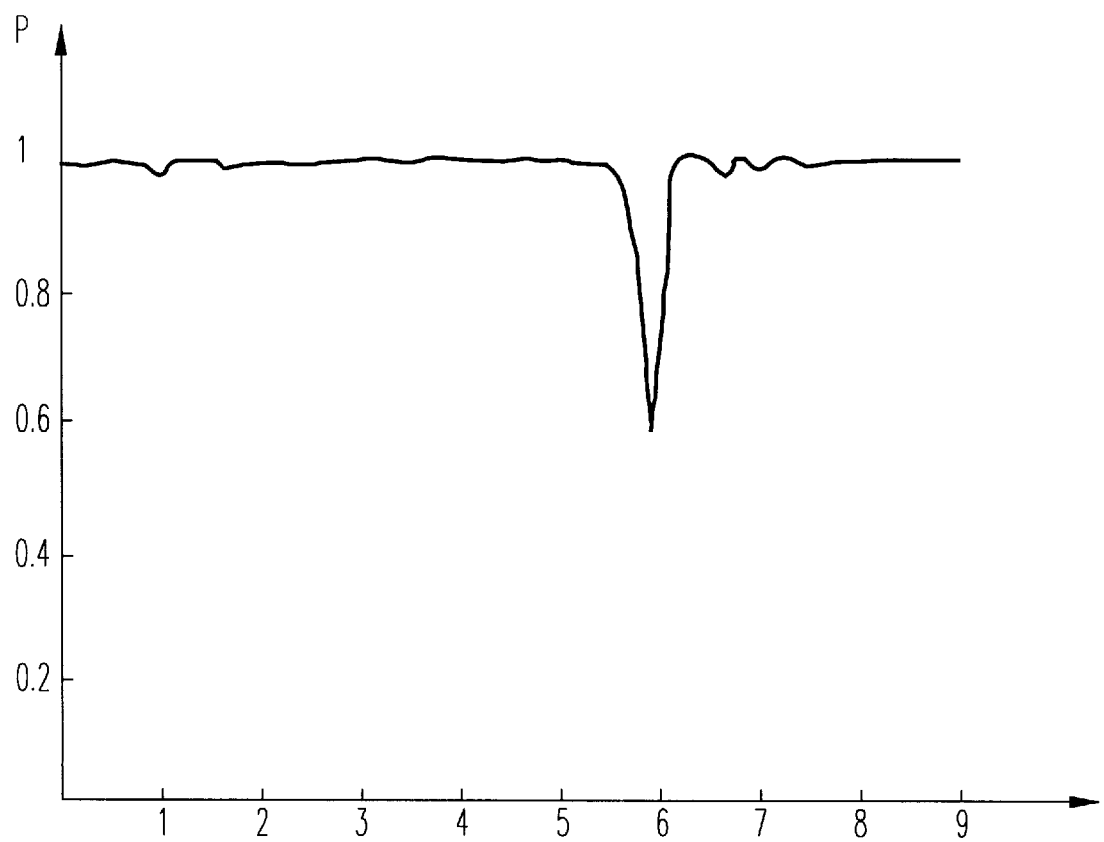
FIG. 2 represents the evolution over time of a first criterion of homogeneity of the first and second sets of work spectra.

The variation at a given instant in the value of the first homogeneity criterion P represented in FIG. 2 signifies that the product manufactured at this instant is very different from the products manufactured previously.

Figure 3:
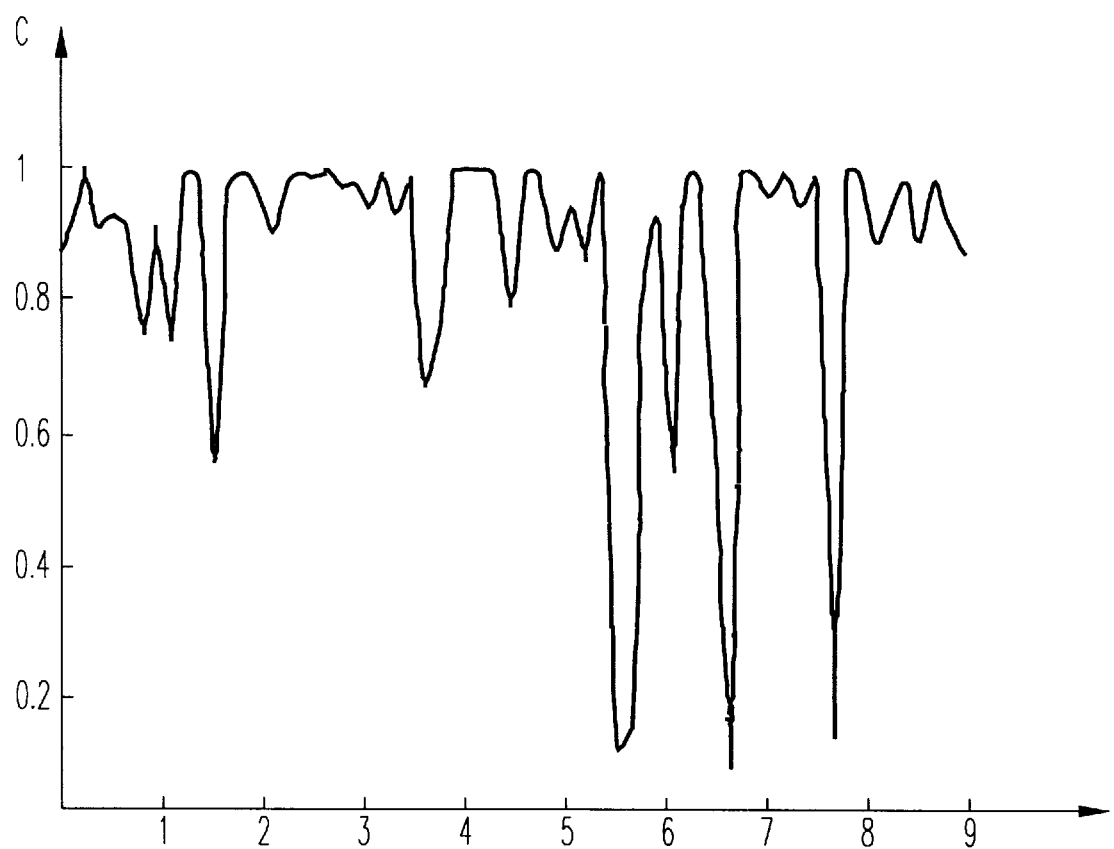
FIG. 3 represents the evolution over time of a second criterion of homogeneity of the first and second sets of work spectra.

The variations, represented in FIG. 3, in the value of the second homogeneity criterion are characteristic of the appearance of variations in the composition of the manufactured product or of disturbances in the operation of the manufacturing unit.

The simultaneous variations in the two homogeneity criteria generate an alarm which alerts the operator running the unit that an incident has occurred.

To track and monitor the operation of the manufacturing unit and/or of the near-infrared spectrometer, use is advantageously made of three univariate control charts which track the respective evolutions of the criteria R, P and C over time.

The limit values used in these control charts are determined experimentally as a function of an evolution profile deemed acceptable by the operator of the manufacturing unit, taking into account for example the confidence interval of the determined characteristic of the manufactured product, that is to say of the engine octane number of the petrol produced.

The anomalies thus exposed are analysed by means of a causes/effects diagram so as to search for the origin thereof, that is to say a malfunction of the manufacturing unit or of the spectrometer or abnormal variation of the composition of the manufactured product.

By virtue of the displaying of the quality criteria, it is possible to detect a malfunction very early and to take corrective measures to prevent the characteristics of the manufactured product from departing from the limits of specifications.

Another advantage of the invention is to allow the enrichment of the learning base used to devise the model, so that this base is homogeneous with a production, adaptable and devoid of spectra related to problems of operation.

I claim:

1. Process for tracking and monitoring the operation of a unit for manufacturing a product and/or a near-infrared spectrometer fed with said product, said spectrometer delivering spectra consisting of series of values of absorbance for various values of wavelengths, consisting in executing the following steps:

periodically recording, in the form of numerical data, spectra arising from the near-infrared spectrometer, mathematically transforming the numerical data of each recorded spectrum so as to obtain transformed spectra, characterized in that it consists in executing the following steps also:

constructing a string of work spectra from the values previously obtained, by choosing wavelengths in each transformed spectrum, by a method of selection, selecting from the string of work spectra, a first set of work spectra containing from 20 to 50 consecutive spectra, selecting from the string of work spectra, a second set of work spectra, of the same dimension as the first set, said spectra being consecutive and shifted in time with respect to the spectra of the first set, computing at least one quality criterion so as to intercompare the first and second sets of spectra, tracking the evolution of said quality criterion over time.

2. Process according to claim 1 characterized in that the method of selection of the wavelengths of the work spectra is chosen from among the method of stepwise selection, the method of selection by elimination, a method applying a regression algorithm and a method implementing genetic algorithms.

3. Process according to claim 2, characterized in that the first set of work spectra comprises spectra obtained from reference products with known characteristics.

4. Process according to claim 2, characterized in that the first set of work spectra containing a first spectrum, the second set of work spectra consists of the same spectra as the first set, except for the first which is replaced with a spectrum not belonging to the first set.

5. Process according to claim 2, characterized in that the spectra of the first and second sets of work spectra being made up of numerical data, the quality criterion is a criterion of representativity of said data, which implements a metric characterizing a distance between said sets.

6. Process according to claim 2, characterized in that the spectra of the first and second sets of work spectra being made up of numerical data, the quality criterion is a first criterion of homogeneity of said data comparing on the one hand the shapes and on the other hand the orientations of said sets.

7. Process according to claim 2, characterized in that the spectra of the first and second sets of work spectra being made up of numerical data, the quality criterion is a second criterion of homogeneity of said data intercomparing the densities of said numerical data.

8. Process according to claim 1 characterized in that, the first set of work spectra comprises spectra obtained from reference products with known characteristics.

9. Process according to claim 8, characterized in that the first set of work spectra containing a first spectrum, the second set of work spectra consists of the same spectra as the first set, except for the first which is replaced with a spectrum not belonging to the first set.

10. Process according to claim 8, characterized in that the spectra of the first and second sets of work spectra being made up of numerical data, the quality criterion is a criterion of representativity of said data, which implements a metric characterizing a distance between said sets.

11. Process according to claim 8, characterized in that the spectra of the first and second sets of work spectra being made up of numerical data, the quality criterion is a first criterion of homogeneity of said data comparing on the one hand the shapes and on the other hand the orientations of said sets.

12. Process according to one of claim 1, characterized in that, the first set of work spectra containing a first spectrum, the second set of work spectra consists of the same spectra as the first set, except for the first which is replaced with a spectrum not belonging to the first set.

13. Process according to claim 12, characterized in that the spectra of the first and second sets of work spectra being made up of numerical data, the quality criterion is a criterion of representativity of said data, which implements a metric characterizing a distance between said sets.

14. Process according to claim 12, characterized in that the spectra of the first and second sets of work spectra being made up of numerical data, the quality criterion is a first criterion of homogeneity of said data comparing on the one hand the shapes and on the other hand the orientations of said sets.

15. Process according to claim 1 characterized in that the spectra of the first and second sets of work spectra being made up of numerical data, the quality criterion is a criterion of representativity of said data, which implements a metric characterizing a distance between said sets.

16. Process according to claim 15 characterized in that the quality criterion is a global criterion computed via a formula involving at least two criteria chosen from among the criterion of representativity, the first criterion of homogeneity and the second criterion of homogeneity.

17. Process according to claim 1 characterized in that the spectra of the first and second sets of work spectra being made up of numerical data, the quality criterion is a first criterion of homogeneity of said data comparing on the one hand the shapes and on the other hand the orientations of said sets.

18. Process according to claim 1 characterized in that the spectra of the first and second sets of work spectra being made up of numerical data, the quality criterion is a second criterion of homogeneity of said data intercomparing the densities of said numerical data.

19. Process according to claim 1 characterized in that in order to track the evolution over time of the quality criterion, a monovariate control chart is used.

20. Process according to claim 1 characterized in that in order to track the evolution over time of the quality criterion, a causes/effects diagram is used.

* * * * *